United States Patent
Shigeta

(10) Patent No.: US 12,020,350 B2
(45) Date of Patent: Jun. 25, 2024

(54) IMAGE PROCESSING APPARATUS

(71) Applicant: FUJIFILM Corporation, Tokyo (JP)

(72) Inventor: Norimasa Shigeta, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 270 days.

(21) Appl. No.: 17/455,117

(22) Filed: Nov. 16, 2021

(65) Prior Publication Data

US 2022/0076458 A1 Mar. 10, 2022

Related U.S. Application Data

(63) Continuation of application No. PCT/JP2020/019511, filed on May 15, 2020.

(30) Foreign Application Priority Data

May 23, 2019 (JP) ................................. 2019-096512

(51) Int. Cl.
*G06T 15/00* (2011.01)
*A61B 1/00* (2006.01)
(Continued)

(52) U.S. Cl.
CPC ........ *G06T 11/001* (2013.01); *A61B 1/00045* (2013.01); *A61B 1/04* (2013.01);
(Continued)

(58) Field of Classification Search
CPC ....... G06T 11/001; G06T 7/0012; G06T 7/40; G06T 7/90; G06T 2207/30096;
(Continued)

(56) References Cited

U.S. PATENT DOCUMENTS

2012/0157768 A1 6/2012 Saito
2012/0220840 A1 8/2012 Morita et al.
(Continued)

FOREIGN PATENT DOCUMENTS

JP S56-95030 A 8/1981
JP 2006-116153 A 5/2006
(Continued)

OTHER PUBLICATIONS

Jha D, Ali S, Hicks S, Thambawita V, Borgli H, Smedsrud PH, de Lange T, Pogorelov K, Wang X, Harzig P, Tran MT. A comprehensive analysis of classification methods in gastrointestinal endoscopy imaging. Medical image analysis. May 1, 2021;70:102007.*
(Continued)

*Primary Examiner* — Phu K Nguyen
(74) *Attorney, Agent, or Firm* — Studebaker & Brackett PC

(57) ABSTRACT

A processor device that is an image processing apparatus functions as an image obtaining unit that obtains an endoscopic image obtained by capturing an image of a photographic subject, a biological information calculation unit that calculates biological information concerning the photographic subject by using the endoscopic image or a display image generated by using the endoscopic image, and a texture processing unit that superimposes a plurality of textures representing the biological information on the endoscopic image or the display image and shows a boundary between adjacent textures.

10 Claims, 10 Drawing Sheets

(51) Int. Cl.
*A61B 1/04* (2006.01)
*G06T 7/40* (2017.01)
*G06T 11/00* (2006.01)

(52) U.S. Cl.
CPC ...... *G06T 7/40* (2013.01); *G06T 2207/10068* (2013.01); *G06T 2210/41* (2013.01)

(58) Field of Classification Search
CPC .... G06T 2207/30101; A61B 1/000094; A61B 1/04; A61B 1/045; A61B 1/00045
USPC .......................................................... 345/418
See application file for complete search history.

(56) References Cited

U.S. PATENT DOCUMENTS

| | | |
|---|---|---|
| 2013/0113906 A1 | 5/2013 | Saito |
| 2014/0024948 A1 | 1/2014 | Shida et al. |
| 2015/0313517 A1 | 11/2015 | Yamaguchi et al. |
| 2017/0112353 A1 | 4/2017 | Ikemoto et al. |
| 2018/0042468 A1 | 2/2018 | Teramura |
| 2018/0214005 A1 | 8/2018 | Ebata |
| 2022/0354356 A1* | 11/2022 | Weeks ................ G06T 7/0012 |
| 2022/0375114 A1* | 11/2022 | Hunter ................ G06T 7/62 |

FOREIGN PATENT DOCUMENTS

| | | |
|---|---|---|
| JP | 2011-104016 A | 6/2011 |
| JP | 2012-139482 A | 7/2012 |
| JP | 2013-099464 A | 5/2013 |
| JP | 2014-094088 A | 5/2014 |
| JP | 2016-154588 A | 9/2016 |
| JP | 2018-126632 A | 8/2018 |
| WO | 2012/132790 A1 | 10/2012 |
| WO | 2016/175084 A1 | 11/2016 |
| WO | 2017/057574 A1 | 4/2017 |

OTHER PUBLICATIONS

Kaneko K, Yamaguchi H, Saito T, Yano T, Oono Y, Ikematsu H, Nomura S, Sato A, Kojima M, Esumi H, Ochiai A. Hypoxia imaging endoscopy equipped with laser light source from preclinical live animal study to first-in-human subject research. PLoS One. Jun. 10, 2014;9(6):e99055.*

Saito T, Yamaguchi H. Optical imaging of hemoglobin oxygen saturation using a small number of spectral images for endoscopic application. Journal of Biomedical Optics. Dec. 1, 2015;20(12):126011-.*

Khemthongcharoen N, Jolivot R, Rattanavarin S, Piyawattanametha W. Advances in imaging probes and optical microendoscopic imaging techniques for early in vivo cancer assessment. Advanced drug delivery reviews. Jul. 30, 2014;74:53-74.*

International Search Report issued in PCT/JP2020/019511; mailed Jul. 28, 2020.

Written Opinion of the International Searching Authority issued in PCT/JP2020/019511; mailed Jul. 28, 2020.

An Office Action; "Decision of Refusal," mailed by the Japanese Patent Office on Mar. 28, 2023, which corresponds to Japanese Patent Application No. 2021-520774 and is related to U.S. Appl. No. 17/455,117; with English language translation.

An Office Action; "Notice of Reasons for Refusal," mailed by the Japanese Patent Office on Oct. 11, 2022, which Corresponds to Japanese Patent Application No. 2021-520774 and is related to U.S. Appl. No. 17/455,117; with English language translation.

* cited by examiner

IMAGE PROCESSING APPARATUS

CROSS-REFERENCE TO RELATED APPLICATIONS

This application is a Continuation of PCT International Application No. PCT/JP2020/019511 filed on 15 May 2020, which claims priority under 35 U.S.C § 119(a) to Japanese Patent Application No. 2019-096512 filed on 23 May 2019. The above application is hereby expressly incorporated by reference, in its entirety, into the present application.

BACKGROUND OF THE INVENTION

1. Field of the Invention

The present invention relates to an image processing apparatus that performs image processing using a medical image, such as an endoscopic image.

2. Description of the Related Art

In the medical field, for example, examinations using endoscope systems are commonly conducted. Endoscope systems include, for example, an endoscope (scope) that is inserted into a photographic subject, a light source device that generates illumination light with which the photographic subject is illuminated, a processor device that obtains an endoscopic image of the photographic subject by using the endoscope, and a monitor that displays, for example, the endoscopic image.

Currently, endoscope systems that not only capture an image of a photographic subject naturally but also calculate and display biological information of the photographic subject using an endoscopic image are known. For example, an endoscope system that superimposes a pseudocolor image showing hemoglobin index values on a part corresponding to a region of interest is known (JP2006-116153A). An endoscope system that displays a specific region, such as a region in which the oxygen saturation level is less than or equal to a certain value, in a pseudocolor is known (JP2012-139482A (corresponding to US2012/157768A1) and JP2014-094088A (corresponding to US2015/313517A1)). An endoscope system that, in a case of displaying an oxygen saturation level in a pseudocolor, sets the color saturation of a region, in which a position shifts to a large degree, to a lower value is known (JP2013-099464A (corresponding to US2013/113906A1)). An endoscope system that changes a display form in accordance with a reliability level indicating the accuracy of setting of a region of interest is known (JP2011-104016A (corresponding to US2012/220840A1)).

SUMMARY OF THE INVENTION

In a case where biological information, such as an oxygen saturation level, is displayed, a method may be used in which the color of a part of the photographic subject or the entire photographic subject is changed to a pseudocolor corresponding to the biological information. Such a display form using a pseudocolor is advantageous in that the biological information can be quantitatively grasped but has shortcomings in that it may be difficult to grasp the structure of the photographic subject due to pseudocoloring. For example, in a case where a pseudocolor is used for a part of the photographic subject, depending on, for example, the color or color saturation of the pseudocolor, it may be difficult to determine whether the part of the photographic subject is displayed in the actual color of the photographic subject or in a color obtained by pseudocoloring.

An object of the present invention is to provide an image processing apparatus that, in a case of displaying biological information on an image, displays the biological information so as to clearly indicate that the biological information is being displayed.

An image processing apparatus of the present invention is an image processing apparatus including a processor, the processor being configured to obtain an endoscopic image obtained by capturing an image of a photographic subject, calculate biological information concerning the photographic subject by using the endoscopic image or a display image generated by using the endoscopic image, and superimpose a plurality of textures representing the biological information on the endoscopic image or the display image and show a boundary between adjacent textures.

Preferably, the processor is configured to provide a gap between adjacent textures.

Preferably, the textures each have a size corresponding to two pixels or more.

Preferably, the processor is configured to superimpose the textures having colors that correspond to the biological information on the endoscopic image or the display image.

Preferably, the processor is configured to superimpose the textures having sizes that correspond to the biological information on the endoscopic image or the display image.

Preferably, the processor is configured to superimpose the textures having shapes that correspond to the biological information on the endoscopic image or the display image.

Preferably, the processor is configured to superimpose a texture on a part that satisfies a specific condition and superimpose no texture on a part that does not satisfy the specific condition.

Preferably, the processor is configured to superimpose a texture on a part in which a difference or ratio between a reference value determined for the biological information and a value of the calculated biological information satisfies the specific condition.

Preferably, the processor is configured to superimpose a texture on a part in which a rate of change of the biological information is greater than or equal to a reference value.

Preferably, the processor is configured to set positions at each of which a texture is allowed to be superimposed to fixed positions on the endoscopic image or the display image.

Preferably, the processor is configured to specify an upper limit to an area for which the textures are allowed to be superimposed, and to superimpose the textures as long as an area of a region in which the textures are superimposed is less than or equal to the upper limit.

Preferably, the processor is configured to stop a process for superimposing the textures in a case where motion of the photographic subject in the endoscopic image or in the display image stops or in a case where motion of an endoscope that captures the endoscopic image or the display image stops.

The image processing apparatus of the present invention can display, in a case of displaying biological information on an image, the biological information so as to clearly indicate that the biological information is being displayed.

DESCRIPTION OF THE PREFERRED EMBODIMENTS

First Embodiment

Figure 1:
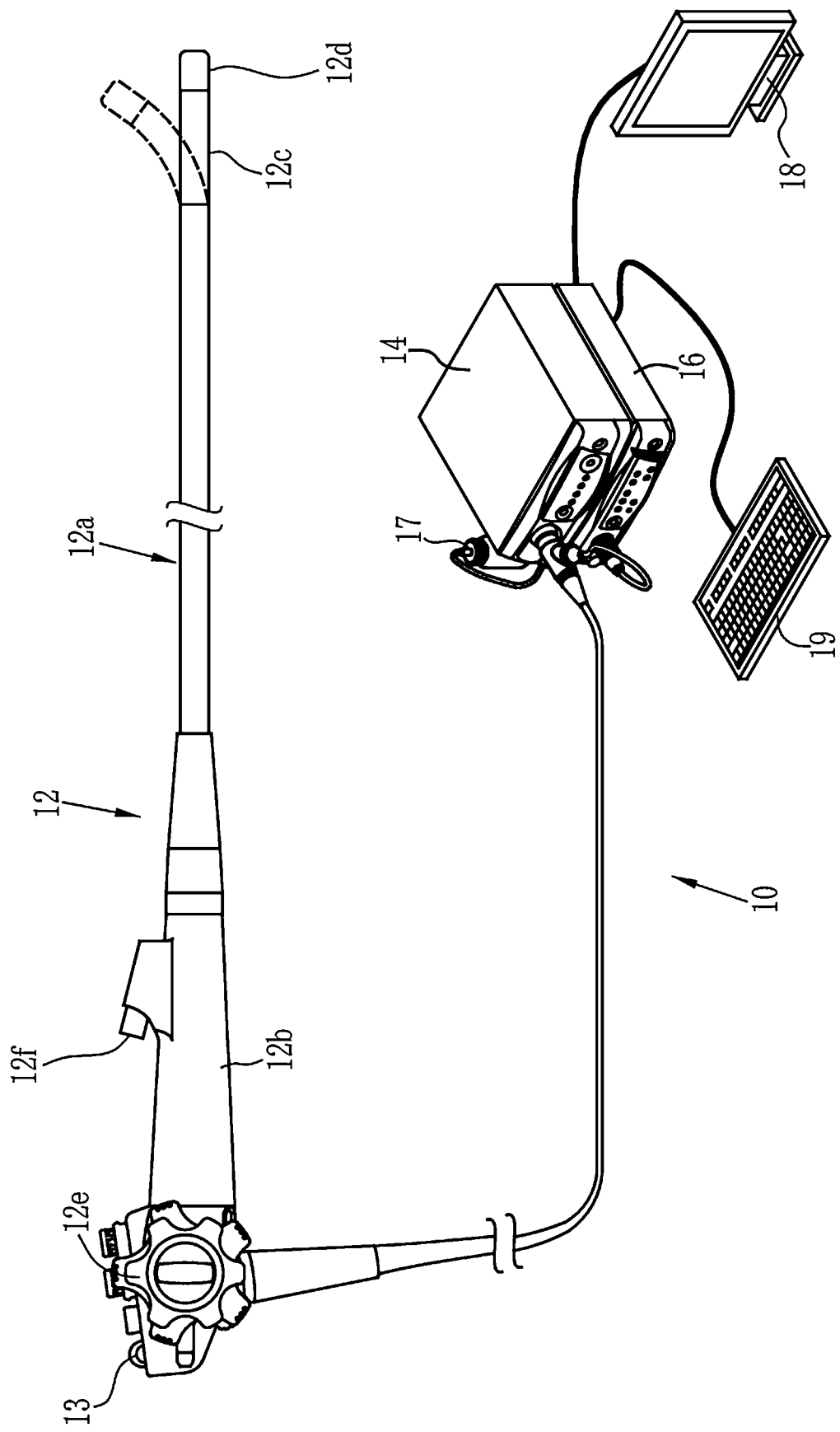
FIG. 1 is an external view of an endoscope system.

As illustrated in FIG. 1, an endoscope system 10 (endoscope apparatus) includes an endoscope 12 (scope), a light source device 14, a processor device 16, a monitor 18, and a console 19. The endoscope 12 captures an image of a photographic subject. The light source device 14 generates illumination light. The processor device 16 performs system control of the endoscope system 10. The processor device 16 generates an endoscopic image and performs image processing for the endoscopic image as necessary. That is, the processor device 16 functions as an image processing apparatus. The monitor 18 is a display unit that displays, for example, an endoscopic image. The console 19 is an input device for, for example, inputting settings to, for example, the processor device 16.

The endoscope 12 has an insertion part 12a that is inserted into a subject, an operation part 12b that is provided on the proximal end part of the insertion part 12a, a bending part 12c that is provided on the distal end side of the insertion part 12a, and a tip part 12d. When an angle knob 12e of the operation part 12b is operated, the bending part 12c bends. As a result, the tip part 12d turns in a desired direction. In addition to the angle knob 12e, the operation part 12b is provided with a treatment tool insertion port 12f and a zoom operation part 13. The treatment tool insertion port 12f is a port through which a treatment tool, such as biopsy forceps, a snare, or an electric scalpel, is inserted. A treatment tool inserted through the treatment tool insertion port 12f protrudes from the tip part 12d. When the zoom operation part 13 is operated, an enlarged or reduced image of a photographic subject is captured.

Figure 2:
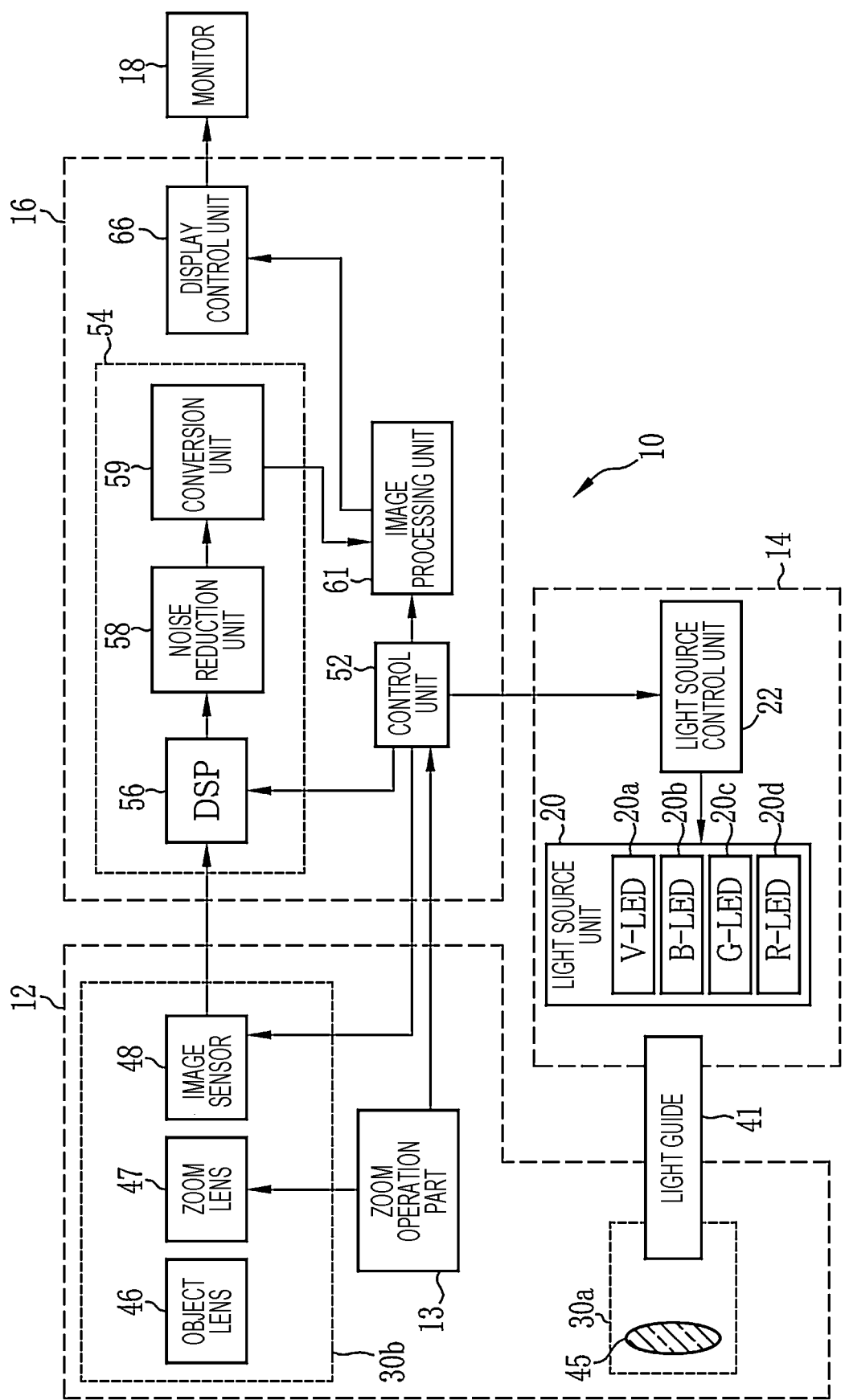
FIG. 2 is a block diagram of the endoscope system.

As illustrated in FIG. 2, the light source device 14 includes a light source unit 20 that emits illumination light and a light source control unit 22 that controls operations of the light source unit 20.

The light source unit 20 emits illumination light that illuminates a photographic subject. Emission of illumination light includes emission of, for example, excitation light that is used to emit illumination light. The light source unit 20 includes a light source formed of, for example, a laser diode, an LED (light emitting diode), a xenon lamp, or a halogen lamp and emits at least illumination light in a white color or excitation light that is used to emit illumination light in the white color. The white color includes a pseudo white color that is substantially equivalent to a white color in image capturing of a photographic subject using the endoscope 12. The light source unit 20 includes, for example, a fluorescent body that emits light when irradiated with excitation light or an optical filter for adjusting, for example, the wavelength range, spectrum, or amount of light of the illumination light or excitation light as necessary. In addition, the light source unit 20 can emit light having a specific wavelength range necessary for capturing an image that is used to calculate biological information, such as the oxygen saturation level of hemoglobin contained in the photographic subject.

In this embodiment, the light source unit 20 has LEDs in four colors, namely, a V-LED 20a, a B-LED 20b, a G-LED 20c, and an R-LED 20d. The V-LED 20a emits violet light VL having a center wavelength of 405 nm and a wavelength range of 380 to 420 nm. The B-LED 20b emits blue light BL having a center wavelength of 460 nm and a wavelength range of 420 to 500 nm. The G-LED 20c emits green light GL having a wavelength range of 480 to 600 nm. The R-LED 20d emits red light RL having a center wavelength of 620 to 630 nm and a wavelength range of 600 to 650 nm. The center wavelengths of the V-LED 20a and the B-LED 20b have a width of about ±20 nm, and preferably, about ±5 nm to about ±10 nm.

The light source control unit 22 controls, for example, the timing at which each light source that constitutes the light source unit 20 is turned on, turned off, or blocked and the amount of light emission of each light source. As a result, the light source unit 20 can emit a plurality of types of illumination light having different spectra. In this embodiment, the light source control unit 22 controls, for example, turning-on and turning-off of each of the LEDs 20a to 20d, the amounts of light emission during turning-on, and insertion and removal of the optical filter by inputting independent control signals to the LEDs 20a to 20d to thereby adjust the spectrum of illumination light. Accordingly, the light source unit 20 emits white light. The light source unit 20 can at least emit illumination light formed of light in a narrow band (hereinafter referred to as narrowband light). "Narrow band" means a substantially single wavelength range in relation to the characteristics of the photographic subject and/or the spectral characteristics of color filters of an image sensor 48. For example, in a case where light has a wavelength range of, for example, about ±20 nm or less (preferably, about ±10 nm or less), the light is in a narrow band. A broad band means a wavelength range relatively broader than that of light in a narrow band in relation to the characteristics of the photographic subject and/or the spectral characteristics of the color filters of the image sensor 48. Therefore, in a case where light has a wavelength range of, for example, ±20 nm or more, the light is light in a broad band.

The light emitted from each of the LEDs 20a to 20d is incident on a light guide 41. The light guide 41 propagates light to the tip part 12d of the endoscope 12. In the tip part 12d of the endoscope 12, an illumination optical system 30a and an imaging optical system 30b are provided. The illumination optical system 30a has an illumination lens 45, and illumination light is emitted toward a photographic subject via the illumination lens 45.

The imaging optical system 30b has an object lens 46, a zoom lens 47, and the image sensor 48. The image sensor 48 captures an image of a photographic subject by using, for example, reflected light (in addition to the reflected light, scattered light, fluorescent light emitted from the photographic subject, or fluorescent light caused by a drug administered to the photographic subject is included) resulting from illumination light and returning from the photographic subject via the object lens 46 and the zoom lens 47. The zoom lens 47 moves in response to an operation of the zoom operation part 13 to enlarge or reduce an image of the photographic subject.

The image sensor 48 has, for each pixel, a color filter in one color among color filters in a plurality of colors. In this embodiment, the image sensor 48 is a color sensor having color filters in primary colors. Specifically, the image sensor 48 has R pixels each having a red filter (R filter), G pixels each having a green filter (G filter), and B pixels each having a blue filter (B filter).

Note that as the image sensor 48, a CCD (charge-coupled device) sensor or a CMOS (complementary metal-oxide semiconductor) sensor can be used. Although the image sensor 48 of this embodiment is a primary color sensor, a complementary color sensor can also be used. A complementary color sensor has, for example, cyan pixels each of which is provided with a cyan filter, magenta pixels each of which is provided with a magenta filter, yellow pixels each of which is provided with a yellow filter, and green pixels each of which is provided with a green filter. In a case where a complementary color sensor is used, an image obtained from the above-described pixels in the respective colors can be converted to an image similar to an image obtained by using a primary color sensor by performing conversion from complementary colors to primary colors. The same applies to a primary color sensor or a complementary color sensor having one or more types of pixels including W pixels (white pixels that receive light in substantially all wavelength ranges) having characteristics other than the above. Although the image sensor 48 of this embodiment is a color sensor, a monochrome sensor having no color filters may be used.

The processor device 16 includes a control unit 52 (processor). The control unit 52 is a hardware resource for executing program instructions stored in a memory not illustrated. The control unit 52 executes the program instructions to thereby cause the processor device 16 to function as an image obtaining unit 54, an image processing unit 61, and a display control unit 66. The control unit 52 executes the program instructions to thereby cause the processor device 16 to also function as an image generation unit 71, a biological information calculation unit 72, and a texture processing unit 73.

The control unit 52 centrally controls the endoscope system 10 and controls, for example, synchronization between the timing of irradiation with illumination light and the timing of image capturing. In a case where, for example, various settings are input by using, for example, the console 19, the control unit 52 inputs the settings to units of the endoscope system 10, such as the light source control unit 22, the image sensor 48, and the image processing unit 61.

The image obtaining unit 54 obtains an endoscopic image obtained by capturing an image of a photographic subject. More specifically, the image obtaining unit 54 obtains from the image sensor 48 an image obtained by image capturing of a photographic subject using the pixels in the respective colors, that is, a raw image. The raw image is an image (endoscopic image) that is not yet subjected to demosaicing. An image obtained from the image sensor 48 and subjected to a process, such as a noise reducing process, is also a raw image as long as the image is not yet subjected to demosaicing.

The image obtaining unit 54 includes a DSP (digital signal processor) 56, a noise reduction unit 58, and a conversion unit 59 that perform various processes for the obtained raw image as necessary to generate an endoscopic image.

The DSP 56 includes, for example, an offset processing unit, a defect correction processing unit, a demosaicing processing unit, a linear matrix processing unit, and a YC conversion processing unit (none of which are illustrated). The DSP 56 uses these units to perform various processes for a raw image or an image generated by using a raw image.

The offset processing unit performs an offset process for a raw image. The offset process is a process for reducing dark current components in a raw image to set an accurate zero level. The offset process may be called a clamping process. The defect correction processing unit performs a defect correction process for a raw image. The defect correction process is a process for, in a case where the image sensor 48 includes a pixel (defective pixel) having a defect caused by a manufacturing process or by aging, correcting or generating the pixel value of a raw pixel corresponding to the defective pixel of the image sensor 48. The demosaicing processing unit performs a demosaicing process for raw images in the respective colors corresponding to the respective color filters. The demosaicing process is a process for generating a pixel value, of a raw image, that is missing due to the arrangement of the color filters, by interpolation. The linear matrix processing unit performs a linear matrix process for an endoscopic image generated by allocating one or more raw images to R, G, and B channels. The linear matrix process is a process for increasing the color reproducibility of the endoscopic image. The YC conversion processing unit performs a YC conversion process that is a process for converting the endoscopic image generated by allocating one or more raw images to the R, G, and B channels to an endoscopic image having a luminance channel Y, a color difference channel Cb, and a color difference channel Cr.

The noise reduction unit 58 performs a noise reduction process for the endoscopic image having the luminance channel Y, the color difference channel Cb, and the color difference channel Cr by using, for example, a moving average method or a median filtering method. The conversion unit 59 reconverts the endoscopic image having the luminance channel Y, the color difference channel Cb, and the color difference channel Cr and subjected to the noise reduction process to an endoscopic image having the channels of the respective colors of R, G, and B.

Figure 3:
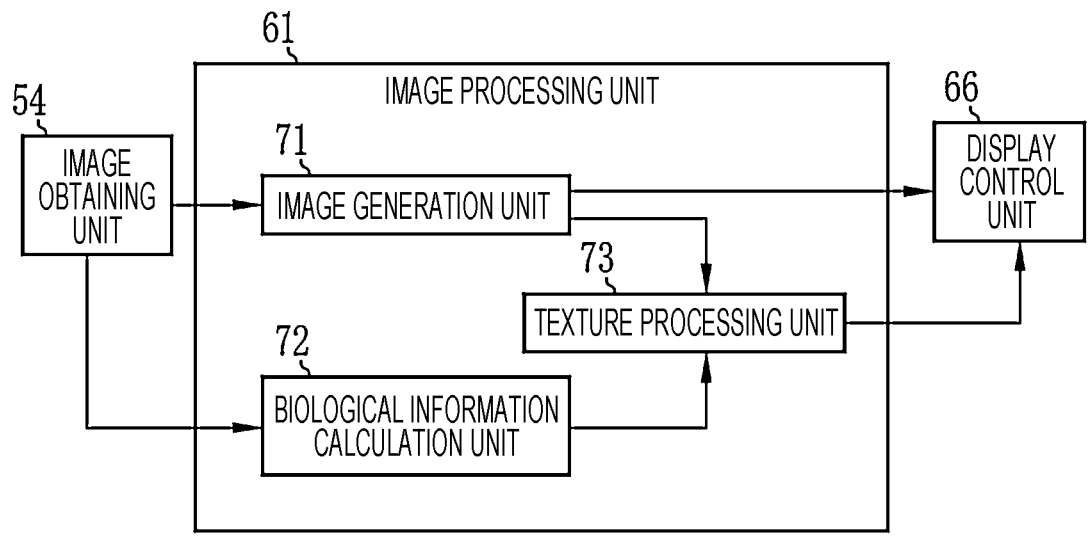
FIG. 3 is a block diagram of an image processing unit.

The image processing unit 61 performs necessary image processing for an endoscopic image output by the image obtaining unit 54. The image processing unit 61 uses the endoscopic image output by the image obtaining unit 54 or another endoscopic image generated by using the endoscopic image output by the image obtaining unit 54 to perform calculation. Specifically, as illustrated in FIG. 3, the image processing unit 61 includes, for example, the image generation unit 71, the biological information calculation unit 72, and the texture processing unit 73.

The image generation unit 71 obtains an endoscopic image from the image obtaining unit 54 and generates an endoscopic image (hereinafter referred to as a display image) that is used in display on, for example, the monitor 18. For example, the image generation unit 71 obtains from the image obtaining unit 54 a B image obtained by image capturing of a photographic subject using the B pixels, a G image obtained by image capturing of the photographic subject using the G pixels, and an R image obtained by image capturing of the photographic subject using the R pixels and uses all or some of these images to generate a display image. Generation of a display image performed by the image generation unit 71 includes, in addition to using a plurality of endoscopic images and obtaining an endoscopic image different from these endoscopic images as described above, performing necessary image processing for one endoscopic image obtained from the image obtaining unit 54 and outputting the endoscopic image, and outputting one endoscopic image obtained from the image obtaining unit 54 as is in its original form.

When generating a display image, the image generation unit 71 performs necessary image processing for an endoscopic image obtained from the image obtaining unit 54 or for a display image generated by using the endoscopic image obtained from the image obtaining unit 54. The image processing performed by the image generation unit 71 is, for example, a highlighting process of highlighting the photographic subject or part of the photographic subject. Highlighting means distinguishing a specific part from, for example, the other tissue or structures so as to allow information about the specific part to be obtained. For example, a process for outlining a part having specific characteristics with a frame to show the outline or a process for, for example, changing the color or luminance of the part having specific characteristics relative to the other parts (for example, a normal mucous membrane) is the highlighting process.

The biological information calculation unit 72 uses an endoscopic image obtained from the image obtaining unit 54 and/or a display image that is an endoscopic image generated by the image generation unit 71 using the endoscopic image obtained from the image obtaining unit 54 to calculate biological information concerning the photographic subject. The biological information is a numerical value or the like indicating overall or partial characteristics of the photographic subject and is, for example, the oxygen saturation level, the blood concentration, the blood vessel density, or the probability that, for example, a lesion or a potential lesion (including a target of a biopsy) has a specific form.

In this embodiment, the biological information calculation unit 72 uses an endoscopic image obtained from the image obtaining unit 54 to calculate the oxygen saturation level of a photographic subject for each pixel. The biological information calculation unit 72 can calculate the oxygen saturation level by using a B image obtained by image capturing of the photographic subject using narrowband light having a wavelength of about 470 nm, a G image obtained by image capturing of the photographic subject using green light in a broad band, and an R image obtained by image capturing of the photographic subject using red light in a broad band. More specifically, the biological information calculation unit 72 calculates, for each pixel, the ratio (hereinafter referred to as B/G) between the B image and the G image described above and the ratio (hereinafter referred to as R/G) between the R image and the G image described above. For example, a table in which B/G and R/G are associated with a value of the oxygen saturation level in accordance with, for example, an experiment or simulation is prepared in advance. The biological information calculation unit 72 calculates the oxygen saturation level from the calculated values of B/G and R/G by using the table. In a case where the biological information calculation unit 72 calculates the oxygen saturation level, the image obtaining unit 54 obtains and provides to the biological information calculation unit 72 the above-described images.

The texture processing unit 73 superimposes a plurality of textures representing biological information on an endoscopic image obtained from the image obtaining unit 54 or a display image generated by the image generation unit 71 (hereinafter referred to as a display image or the like). The texture processing unit 73 superimposes textures on the endoscopic image in a case where, for example, the endoscopic image is used in, for example, display. That is, a target on which the texture processing unit 73 superimposes textures is an image to be displayed on, for example, the monitor 18. Hereinafter, a display image or the like on which the texture processing unit 73 superimposes textures is referred to as a biological information image. The biological information image is an image (endoscopic image) that shows biological information with the textures.

"Showing biological information" means adjusting or changing the display form directly on the basis of values of the biological information calculated by the biological information calculation unit 72 or indirectly on the basis of numerical values or the like that are, for example, calculated by using the biological information, and includes showing the shape, position, size, and/or area of a part in which, for example, the biological information has a value that satisfies a specific condition, in addition to showing values of the biological information or numerical values or the like that are, for example, calculated by using the biological information.

A texture is, for example, a geometric shape (including a geometric shape having the form of letter or symbol) that is superimposed on a part of a display image or the like and that has a specific pattern and/or shape (outline). A texture can be formed of a line that outlines the shape of, for example, a geometric shape (an outline shape). The shape of a texture might not be clearly recognizable in a display image or the like because, for example, the texture has a gradation pattern having different colors depending on the position. In this embodiment, a texture used by the texture processing unit 73 is a tile texture 85 (see, for example, FIG. 4) that is a rectangular geometric shape and has a colored inner part.

"Superimposing" a texture on a display image or the like means, at least in a case of displaying a display image or the like on, for example, the monitor 18, superimposing on a display image or the like and displaying a texture such that features of the texture, such as the pattern, shape, and/or color, can be recognized so as to be distinguishable from the photographic subject present in the display image or the like, and includes combining (integrating) the texture with (into) the display image or the like, in addition to superimposing on the display image or the like and displaying the texture so as to be separable. In this embodiment, the texture processing unit 73 superimposes a texture on a display image or the like so as to be separable.

The texture processing unit 73 has a plurality of types of textures having different shapes, colors, patterns, or sizes and can select and use one type of texture among the plurality of types of textures on the basis of a setting or the like. The texture processing unit 73 can use a combination of the plurality of types of textures on the basis of a setting or the like.

In addition, the texture processing unit 73 can superimpose on a display image or the like, each texture while changing, for example, the size, color (for example, hue, brightness, and color saturation), luminance, and/or transparency of some or all of the elements of the texture. Note that the texture processing unit 73 sets the size of each texture to at least two pixels or more of the display image or the like on which the texture is superimposed in order to clearly differentiate the texture from pixels of the display image or the like and to allow the texture to be recognized as a texture. The texture processing unit 73 sets the size of each texture to a size that is smaller than a display image or the like on which the texture is superimposed and with which at least two or more textures can be superimposed and displayed within a photographic subject display area 83 (see FIG. 4) in order for the texture to exhibit a function of representing biological information. In a case of superimposing a plurality of textures on a display image or the like, the texture processing unit 73 can superimpose the textures on the display image or the like while relatively changing, for example, the sizes, colors, luminances, and/or transparencies of the textures.

A form in which the texture processing unit 73 superimposes textures on a display image or the like is a form in which, in a case of superimposing the plurality of textures on the display image or the like, the boundary between textures that are superimposed at positions adjacent to each other on the display image or the like (hereinafter referred to as adjacent textures) is shown. "Showing the boundary" means displaying the textures such that the patterns or shapes of the textures are distinguishably perceived on the display image or the like. For example, a form in which a gap is provided between adjacent textures is a form in which the boundary is shown. In a case where adjacent textures share the outline or in a case where adjacent textures overlap partially or entirely, when the textures can be distinguished from each other on the basis of, for example, the patterns of the textures or the colors of the outlines of the textures, such a form is a form in which the boundary is shown. In this embodiment, the texture processing unit 73 provides a gap between adjacent textures (see, for example, FIG. 4).

In addition, the texture processing unit 73 sets positions at each of which a texture can be superimposed to specific positions on a display image or the like. That is, the texture processing unit 73 sets in advance positions at each of which a texture can be superimposed, in accordance with, for example, the display size of the display image or the like regardless of, for example, the shape of the photographic subject. Further, the texture processing unit 73 superimposes a texture on a part that satisfies a specific condition and superimposes no texture on a part that does not satisfy the specific condition.

Specifically, the texture processing unit 73 sets a plurality of lattice points for identifying positions at each of which a texture can be superimposed on a display image or the like, on the basis of a setting or the like. The texture processing unit 73 superimposes textures at necessary positions of some or all of the lattice points at each of which a texture can be superimposed, on the basis of biological information to be displayed. The texture processing unit 73 sets the lattice points independently of the shape of the photographic subject. The texture processing unit 73 does not change the positions and distribution (for example, density) of the lattice points on a display image or the like in accordance with a change in the photographic subject present on the display image or the like. That is, the positions at each of which a texture can be superimposed do not follow a change in, for example, the shape of the photographic subject but are fixed. However, whether the texture processing unit 73 superimposes a texture on each lattice point depends on a change in the photographic subject. This is because, for example, values of biological information calculated by the biological information calculation unit 72 change by following a change in the photographic subject.

Figure 4:
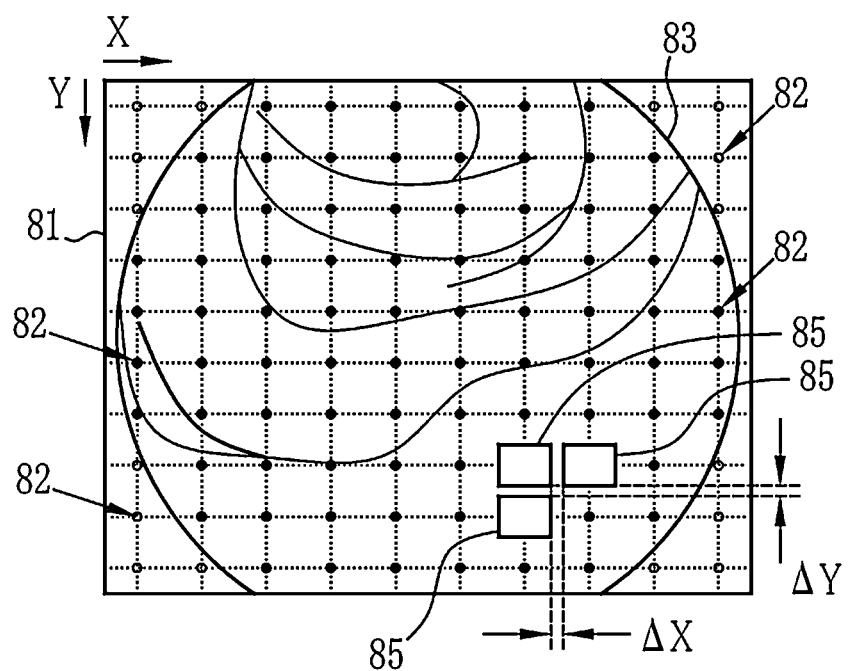
FIG. 4 is an explanatory diagram illustrating textures and lattice points on each of which a texture can be superimposed.

In this embodiment, as illustrated in FIG. 4, the texture processing unit 73 sets lattice points 82 in a square lattice on a display image 81. Among the lattice points 82, the lattice point 82 that is within the photographic subject display area 83 in which the photographic subject is displayed is assumed to be a position at which a texture can be superimposed. In FIG. 4, the lattice point 82 that is within the photographic subject display area 83 is indicated by a filled small circle (•) and the lattice point 82 that is outside the photographic subject display area 83 is indicated by an outlined small circle (∘).

The arrangement (type of lattice) and density (interval) of the lattice points 82 can be changed as desired on the basis of a setting or the like. The texture processing unit 73 may automatically change, for example, the size and/or shape of textures in accordance with the arrangement and density of the lattice points 82 in order to appropriately show the boundaries between the textures. In this embodiment, the texture processing unit 73 superimposes each tile texture 85 on the display image 81 such that the center (center position) of the tile texture 85 corresponds to a corresponding one of the lattice points 82. The texture processing unit 73 adjusts the size of each tile texture 85 to provide a gap $\Delta X$ in the X direction and provide a gap $\Delta Y$ in the Y direction. The gap in the X direction ($\Delta X$) and the gap in the Y direction ($\Delta Y$) may be equal to each other or different from each other. In this embodiment, the gap in the X direction ($\Delta X$) and the gap in the Y direction ($\Delta Y$) are equal to each other in order to reduce the directional characteristics of the gaps between the tile textures 85 and to prevent, for example, an unintended shape or pattern from appearing on the display image 81 due to the directional characteristics of the gaps between the tile textures 85.

The texture processing unit 73 obtains biological information from the biological information calculation unit 72 and uses values of the obtained biological information or numerical values or the like calculated by using the biological information to determine, for each lattice point 82, whether to superimpose a texture on the lattice point 82.

In this embodiment, the biological information calculation unit 72 calculates the oxygen saturation level as biological information. Accordingly, the texture processing unit 73 superimposes a texture on a part corresponding to a region in which the oxygen saturation level is less than or equal to a reference value (hereinafter referred to as a low-oxygen region). The reference value is determined in advance for each type of biological information in accordance with the type of biological information. In a case where biological information is the oxygen saturation level, the reference value is, for example, 70%.

More specifically, the texture processing unit 73 uses values of the oxygen saturation level calculated by the biological information calculation unit 72 to calculate the average of the oxygen saturation level for pixels belonging to a specific region that includes each lattice point 82 (for example, the Wigner-Seitz cell of each lattice point 82) and compare the calculated average with the reference value determined in advance. In a case where the average of the oxygen saturation level is less than or equal to the reference value, the texture processing unit 73 determines that the lattice point 82 belongs to a low-oxygen region and superimposes a texture on the lattice point 82. On the other hand, in a case where the average of the oxygen saturation level is greater than the reference value, the texture processing unit 73 determines that the lattice point 82 belongs to a high-oxygen region (a region in which the value of the oxygen saturation level is normal) and decides not to superimpose a texture on the lattice point 82.

Note that although the texture processing unit 73 calculates the average of the oxygen saturation level in this embodiment, the texture processing unit 73 can calculate another statistic, such as the sum total, median, minimum value, variance, or standard deviation, instead of the average and use the other statistic to determine whether to superimpose a texture (hereinafter referred to as superimposition determination). The texture processing unit 73 can calculate a plurality of statistics and use a combination of the statistics in superimposition determination. In addition, the texture processing unit 73 can obtain, for example, the rate of change of the oxygen saturation level (for example, the gradient of the distribution of the oxygen saturation level (derivative value)) and use the rate of change of the oxygen saturation level or a statistic concerning the rate of change of the oxygen saturation level in superimposition determination. In these cases, in accordance with, for example, a statistic used to determine whether to superimpose a texture, the reference value is set in advance to a value that is comparable with the statistic. In a case where a plurality of calculation values, such as statistics and/or derivative values, are used in superimposition determination, a plurality of reference values may be set in accordance with, for example, the respective statistics.

The display control unit 66 converts a display image or the like output by the image processing unit 61 so as to have a format suitable to display and outputs the display image to the monitor 18. Accordingly, the monitor 18 displays the display image. When the texture processing unit 73 superimposes a texture on a display image or the like, the display control unit 66 obtains a biological information image from the texture processing unit 73 and outputs the biological information image to the monitor 18.

Figure 5:
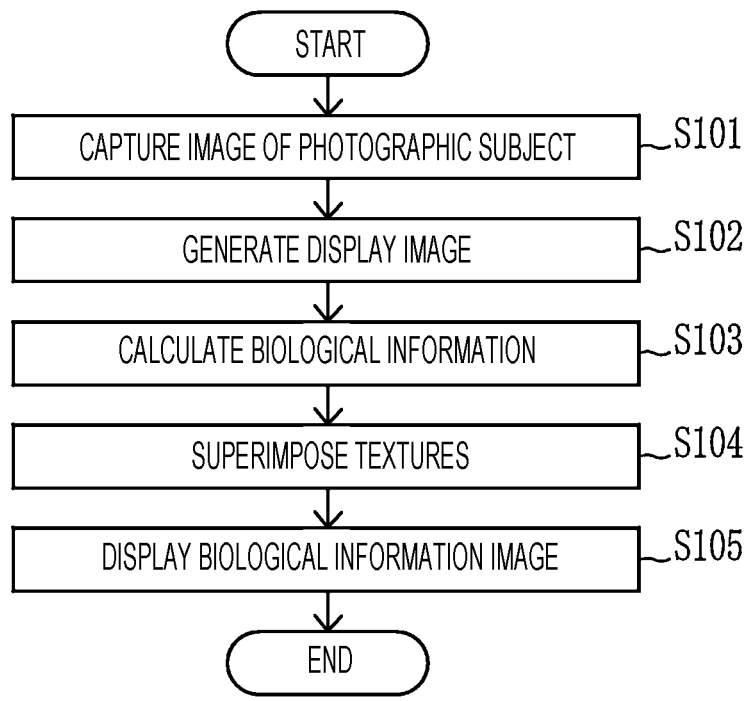
FIG. 5 is a flowchart illustrating a flow of operations of the endoscope system.

Now, operations of the endoscope system 10 configured as described above are described. As illustrated in FIG. 5, when the endoscope 12 is inserted into a photographic subject and image capturing of the photographic subject is started (step S101), the image generation unit 71 obtains an endoscopic image from the image obtaining unit 54 and uses the endoscopic image to generate the display image 81 (step S102). The endoscopic image obtained by the image generation unit 71 is an endoscopic image used in generation of the display image 81 and also an endoscopic image used by the biological information calculation unit 72 to calculate biological information.

Figure 6:
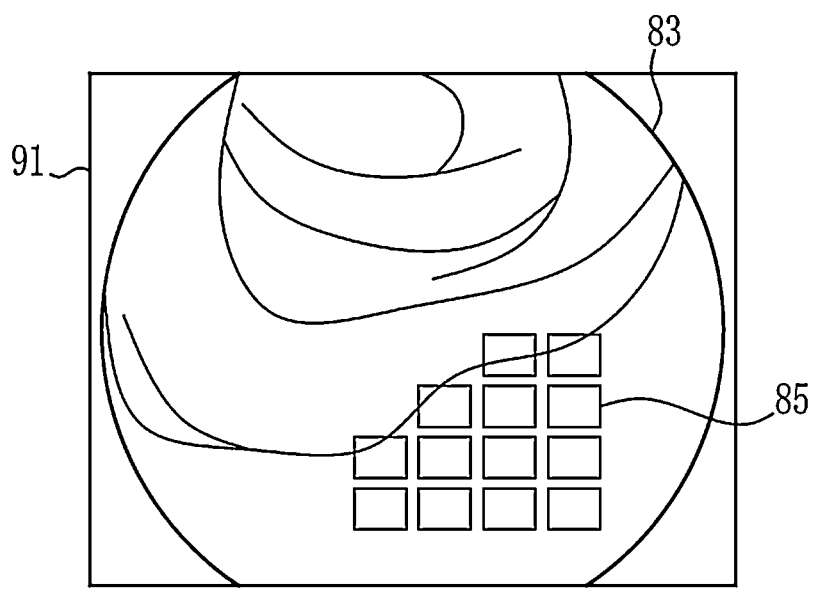
FIG. 6 illustrates a display image showing biological information by superimposing textures.

Meanwhile, the biological information calculation unit 72 obtains the endoscopic image from the image obtaining unit 54 and uses the endoscopic image to calculate the oxygen saturation level, which is biological information, for each pixel (step S103). Thereafter, the texture processing unit 73 uses the oxygen saturation level calculated by the biological information calculation unit 72 to perform superimposition determination for each lattice point 82. Then, as illustrated in FIG. 6, the texture processing unit 73 superimposes, on the display image 81, the tile texture 85, which is one form of texture, on the lattice point 82 that belongs to, for example, a low-oxygen region (step S104) to thereby generate a biological information image 91. As a result, the monitor 18 displays the biological information image 91 (step S105).

Generation and display of the biological information image 91 are repeatedly performed each time an image of the photographic subject is captured with the endoscope 12 or intermittently during the period in which an image of the photographic subject is being captured with the endoscope 12 as long as switching to, for example, an observation mode in which calculation and display of biological information are not performed does not occur.

As described above, the endoscope system 10 calculates biological information by the processor device 16 that functions as an image processing apparatus and uses the biological information image 91 on which textures are superimposed to display the biological information. The textures are superimposed so as to show the boundary between adjacent textures. Accordingly, the endoscope system 10 can display the biological information so as to clearly indicate that the biological information is being displayed. For example, in a case where the color of a part of a display image or the like or the whole display image or the like is changed to a color corresponding to a value of the biological information, it may be difficult to determine whether the color of the changed part is the original color of a living body that is the photographic subject, depending on, for example, the color after the change or the color of the photographic subject. In contrast, the endoscope system 10 or the processor device 16 uses textures and shows the boundary between adjacent textures to thereby provide the impression that the textures are apparently artificial elements. Accordingly, with the biological information image 91, it can be correctly recognized that the textures are additional elements superimposed by image processing (for example, a process for superimposing the textures). As a result, it can be clearly known that the biological information is being displayed.

Figure 7:
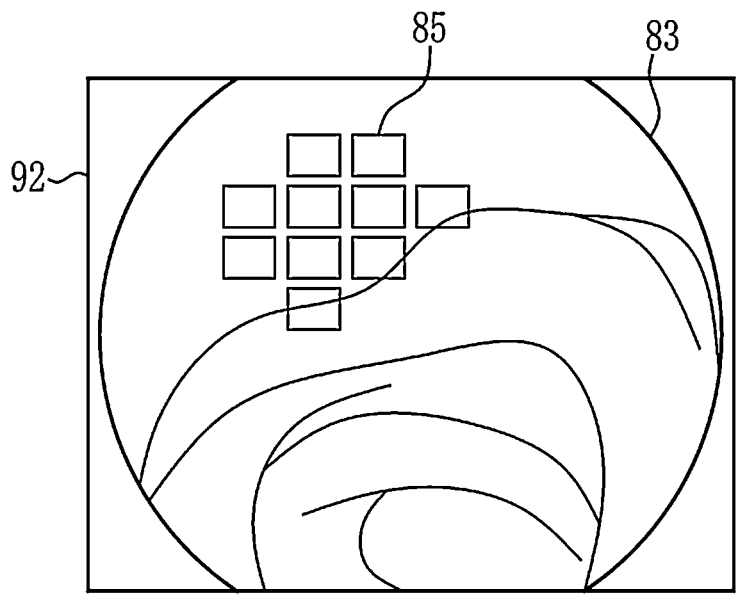
FIG. 7 illustrates a display image and shows a display form of textures in a case where, for example, a photographic subject has moved.

In the first embodiment described above, a gap is provided between adjacent textures, and therefore, the boundary between the textures is apparent. Accordingly, the biological information image 91 can show biological information so as to very clearly indicate that the biological information is being displayed Further, in the first embodiment described above, as long as a setting is not changed, for example, the positions of the lattice points 82 at each of which a texture can be superimposed do not depend on the shape or a change in the photographic subject but are fixed on the display image or the like. Accordingly, the positions at each of which a texture is superimposed move by following a change in the photographic subject, but the form of the movement is discrete and can provide an artificial impression. As a result, biological information can be displayed so as to clearly indicate that the biological information is being displayed. Specifically, in a case where the photographic subject of the biological information image 91 (see FIG. 6) changes as in a biological information image 92 illustrated in FIG. 7, the positions at each of which the tile texture 85 is superimposed move as a whole by following the change in the photographic subject. Meanwhile, discrete (discontinuous) changes in which one tile texture 85 appears at a certain lattice point 82 and one tile texture 85 does not appear at another lattice point 82 occur at once in a macroscopic area (in the entire one texture) for one pixel of the biological information image 91 and of the biological information image 92. Accordingly, a transition of the tile textures 85 has continuity as a whole such that the tile textures 85 move to positions at which biological information is to be displayed, by following a change in the photographic subject. At the same time, the transition can provide the impression of an artificial change that is not smooth unlike the change in the photographic subject, and it is clear that the tile textures 85 are additionally displayed.

In addition, in the above-described embodiment, the texture processing unit 73 superimposes a texture on a part that satisfies a specific condition and superimpose no texture on a part that does not satisfy the specific condition. Accordingly, textures are superimposed partially, and therefore, a part to which attention is to be paid can be appropriately displayed unlike in a case where textures are superimposed on the entire display image or the like.

Further, display with textures in the above-described embodiment is specifically effective in identifying an infiltration portion, presenting a potential target of a biopsy, and/or identifying a region of interest (a region to which attention is to be paid).

Second Embodiment

In the first embodiment described above, the texture processing unit 73 superimposes the same tile textures 85 on the plurality of lattice points 82 respectively to generate, for example, the biological information image 91 (see, for example, FIG. 6). In a case of superimposing the tile textures 85 on the respective lattice points 82, the texture processing unit 73 can change the features of the tile textures 85. Accordingly, it is preferable that the texture processing unit 73 adjust the features of the textures in accordance with biological information. This is because when the features of the textures are adjusted in accordance with biological information, not only a position and/or an area to which attention is to be paid but also the content of biological information (for example, values of biological information) can be made known with the display form of textures.

Figure 8:
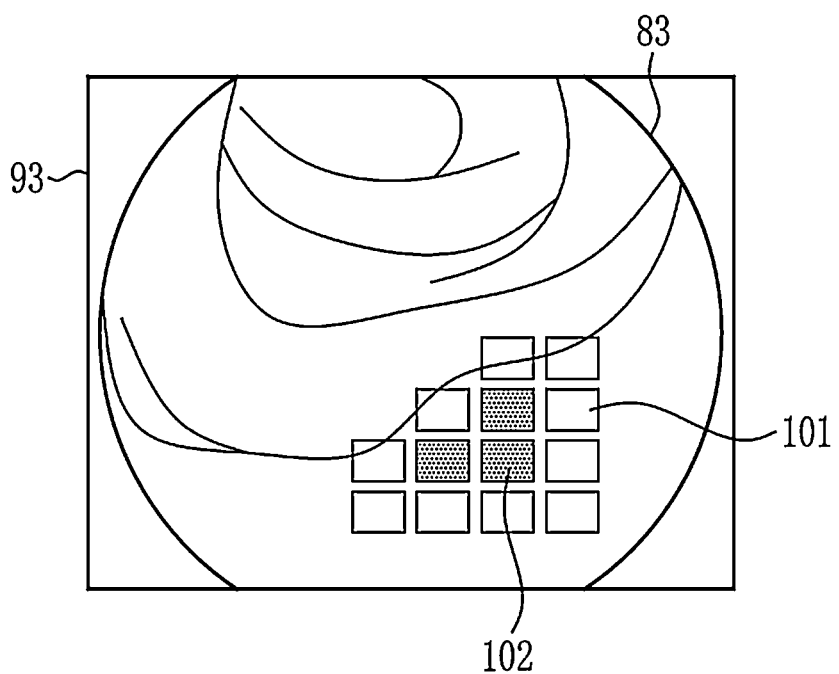
FIG. 8 illustrates a display image in a display form in which the colors of textures are changed in accordance with biological information.

Specifically, it is preferable that the texture processing unit 73 superimpose textures having colors that correspond to biological information on a display image or the like. "Having colors that correspond to biological information" means displaying the degrees of biological information, that is, values of biological information calculated by the biological information calculation unit 72 or numerical values or the like that are, for example, calculated by using the biological information, in colors. For example, as illustrated in FIG. 8, the texture processing unit 73 can generate a biological information image 93 by superimposing, on the basis of the average of the oxygen saturation level in a specific region that includes the lattice point 82 on which a texture is to be superimposed, either a first-color texture 101 or a second-color texture 102 on the lattice point 82. The first-color texture 101 and the second-color texture 102 are originally the tile textures 85. Accordingly, the features of the first-color texture 101 and the second-color texture 102 are the same as those of the tile textures 85 except their colors. The color of the first-color texture 101 is, for example, light blue, and the color of the second-color texture 102 is, for example, dark blue.

As described above, in a case where, for example, values of the oxygen saturation level are displayed in two types of colors, the texture processing unit 73 sets a threshold value for determining the colors in addition to the reference value for determining whether to superimpose a texture on each lattice point 82. For the lattice point 82 on which the texture processing unit 73 decides to superimpose a texture, the texture processing unit 73 compares, for example, the average of the oxygen saturation level with the threshold value to determine the color of the texture to be superimposed. For example, the texture processing unit 73 superimposes the second-color texture 102 on the lattice point 82 for which the average of the oxygen saturation level is less than or equal to the threshold value and superimposes the first-color texture 101 on the lattice point 82 for which the average of the oxygen saturation level is greater than the threshold value. Accordingly, the texture processing unit 73 generates the biological information image 93 from the display image 81.

Although two types of textures, namely, the first-color texture 101 and the second-color texture 102, are used to display values of the oxygen saturation level in two types of colors, the colors of the textures can be changed as desired. Accordingly, the texture processing unit 73 can display, for example, values of the oxygen saturation level in three or more colors by using, in addition to the first-color texture 101 and the second-color texture 102, a texture in a color different from the colors of the first-color texture 101 and the second-color texture 102. In this case, a plurality of threshold values for determining the colors need to be prepared.

Third Embodiment

It is preferable that the texture processing unit 73 superimpose textures having sizes that correspond to biological information on a display image or the like. This is because not only a position and/or an area to which attention is to be paid but also the content of biological information (for example, values of biological information) can be made known with the display form of textures.

Figure 9:
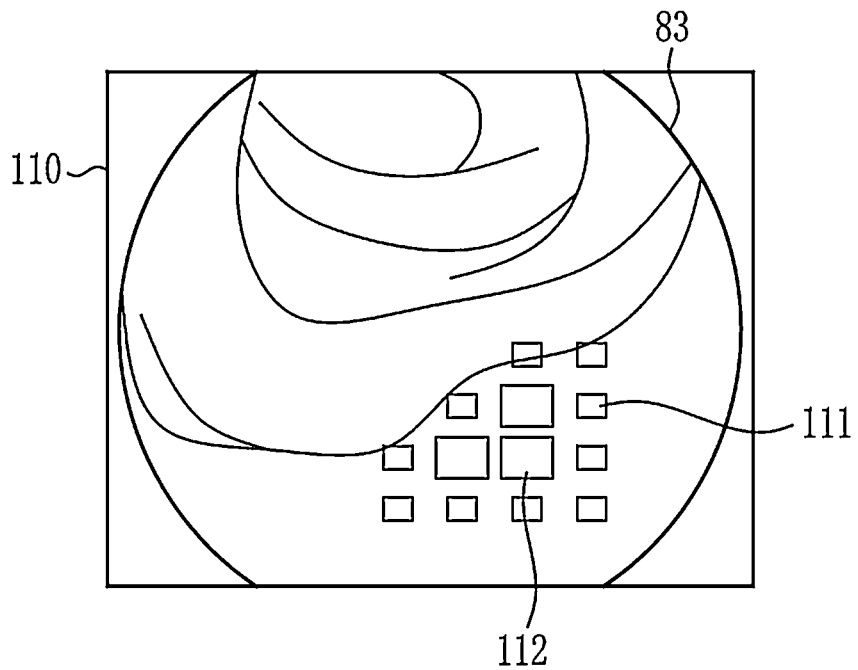
FIG. 9 illustrates a display image in a display form in which the sizes of textures are changed in accordance with biological information.

"Having sizes that correspond to biological information" means displaying the degrees of biological information, that is, values of biological information calculated by the biological information calculation unit 72 or numerical values or the like that are, for example, calculated by using the biological information, with the sizes of textures. For example, as illustrated in FIG. 9, the texture processing unit 73 can generate a biological information image 110 by superimposing, on the basis of the average of the oxygen saturation level in a specific region that includes the lattice point 82 on which a texture is to be superimposed, either a first-size texture 111 or a second-size texture 112 on the lattice point 82. The first-size texture 111 and the second-size texture 112 are originally the tile textures 85. Accordingly, the features of the first-size texture 111 and the second-size texture 112 are the same as those of the tile textures 85 except their sizes. The size of the first-size texture 111 is relatively smaller than the size of the second-size texture 112.

A process that is performed in a case where, for example, values of the oxygen saturation level are displayed with two types of sizes as described above is similar to the process that is performed in a case where the textures are made to have colors that correspond to biological information. That is, the texture processing unit 73 sets a threshold value for determining the sizes of textures in addition to the reference value for determining whether to superimpose a texture on each lattice point 82. For the lattice point 82 on which the texture processing unit 73 decides to superimpose a texture, the texture processing unit 73 compares, for example, the average of the oxygen saturation level with the threshold value to determine the size of the texture to be superimposed. For example, the texture processing unit 73 superimposes the second-size texture 112 on the lattice point 82 for which the average of the oxygen saturation level is less than or equal to the threshold value and superimposes the first-size texture 111 on the lattice point 82 for which the average of the oxygen saturation level is greater than the threshold value. Accordingly, the texture processing unit 73 generates the biological information image 110 from the display image 81.

Although two types of textures, namely, the first-size texture 111 and the second-size texture 112, are used to display values of the oxygen saturation level with two types of texture sizes, the texture sizes can be changed as desired. Accordingly, the texture processing unit 73 can display, for example, values of the oxygen saturation level with three or more texture sizes by using, in addition to the first-size texture 111 and the second-size texture 112, a texture having a size different from the sizes of the first-size texture 111 and the second-size texture 112. In this case, a plurality of threshold values for determining the texture sizes need to be prepared. In a case where textures having a maximum size are respectively superimposed on the lattice points 82 adjacent to each other, it is preferable to set the maximum size of these textures to a size such that the textures do not overlap except their outlines in order to facilitate showing of the boundary between the textures and to clearly indicate with more certainty that the textures represent biological information.

Fourth Embodiment

It is preferable that the texture processing unit 73 superimpose textures having shapes that correspond to biological information on a display image or the like. This is because not only a position and/or an area to which attention is to be paid but also the content of biological information (for example, values of biological information) can be made known with the display form of textures.

Figure 10:
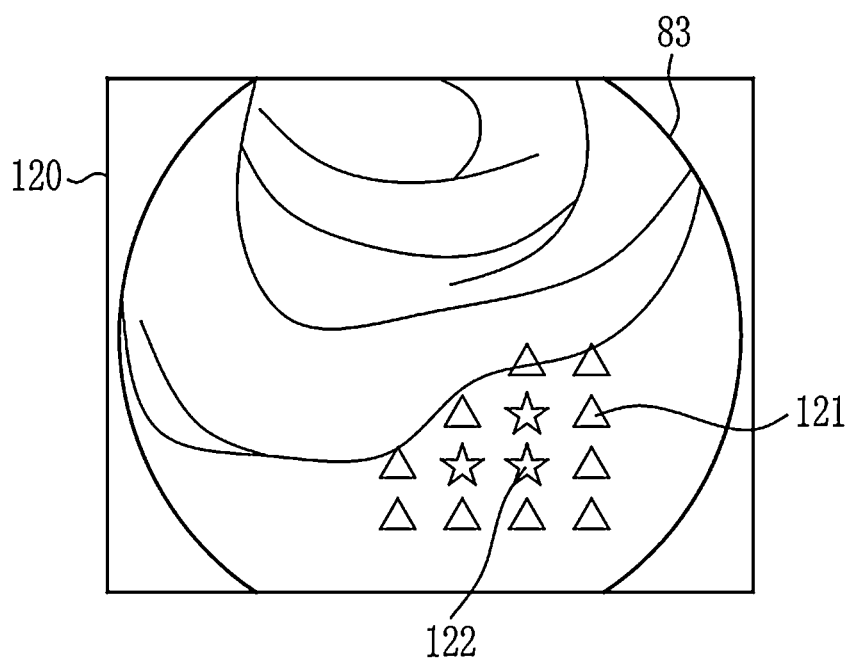
FIG. 10 illustrates a display image in a display form in which the shapes of textures are changed in accordance with biological information.

"Having shapes that correspond to biological information" means displaying the degrees of biological information, that is, values of biological information calculated by the biological information calculation unit 72 or numerical values or the like that are, for example, calculated by using the biological information, with the shapes of, for example, textures or the geometric shapes that form textures. For example, as illustrated in FIG. 10, the texture processing unit 73 can generate a biological information image 120 by superimposing, on the basis of the average of the oxygen saturation level in a specific region that includes the lattice point 82 on which a texture is to be superimposed, either a first-shape texture 121 or a second-shape texture 122 on the lattice point 82. The first-shape texture 121 is, for example, a triangular texture and has features, including the color, the same as those of the tile texture 85 except its shape. The second-shape texture 122 is, for example, a star-shaped texture and has features, including the color, the same as those of the tile texture 85 except its shape.

A process that is performed in a case where, for example, values of the oxygen saturation level are displayed with two types of texture shapes as described above is similar to the process that is performed in a case where the textures are made to have colors that correspond to biological information. That is, the texture processing unit 73 sets a threshold value for determining the sizes of textures in addition to the reference value for determining whether to superimpose a texture on each lattice point 82. For the lattice point 82 on which the texture processing unit 73 decides to superimpose a texture, the texture processing unit 73 compares, for example, the average of the oxygen saturation level with the threshold value to determine the shape of the texture to be superimposed. For example, the texture processing unit 73 superimposes the second-shape texture 122 on the lattice point 82 for which the average of the oxygen saturation level is less than or equal to the threshold value and superimposes the first-shape texture 121 on the lattice point 82 for which the average of the oxygen saturation level is greater than the threshold value. Accordingly, the texture processing unit 73 generates the biological information image 120 from the display image 81.

Although two types of textures, namely, the first-shape texture 121 and the second-shape texture 122, are used to display values of the oxygen saturation level with two types of texture shapes, three or more types of textures having different shapes may be prepared in advance. Accordingly, the texture processing unit 73 can display, for example, values of the oxygen saturation level with three or more texture shapes by using, in addition to the first-shape texture 121 and the second-shape texture 122, a texture (for example, the tile texture 85) having a shape different from the shapes of the first-shape texture 121 and the second-shape texture 122. In this case, a plurality of threshold values for determining the shapes of textures to be superimposed need to be prepared.

Although the shapes of textures are determined on the basis of the degrees of biological information in the fourth embodiment described above, the shapes of textures may be determined on the basis of the types of biological information. For example, in a case where the biological information calculation unit 72 calculates the blood concentration in addition to the oxygen saturation level, the first-shape texture 121 can be used in display of the oxygen saturation level and the second-shape texture 122 can be used in display of the blood concentration. In this case, pieces of information concerning the plurality of types of biological information can be known with a single biological information image without confusion.

The display forms using the textures of the second embodiment, the third embodiment and the fourth embodiment described above can be combined as desired. That is, the texture processing unit 73 can superimpose textures having colors, sizes, and/or shapes that correspond to biological information, on a display image or the like. In this case, the biological information can be displayed so as to clearly indicate that the biological information is being displayed, and the biological information can be displayed in a form that has combined advantages of the second embodiment, the third embodiment, and the fourth embodiment described above.

Fifth Embodiment

In the first embodiment, the second embodiment, the third embodiment, the fourth embodiment, and modifications thereof described above, a gap is provided between adjacent textures to show the boundary. Also in a case where no gap is present between adjacent textures, the boundary can be shown. For example, in a case where textures are superimposed on a display image or the like such that adjacent textures share the boundary without providing a gap between the adjacent textures, the texture processing unit 73 can show the boundary between the adjacent textures, for example, with the features of the respective textures, such as their colors or patterns, or by adding a border line in addition to superimposition of the adjacent textures.

Figure 11:
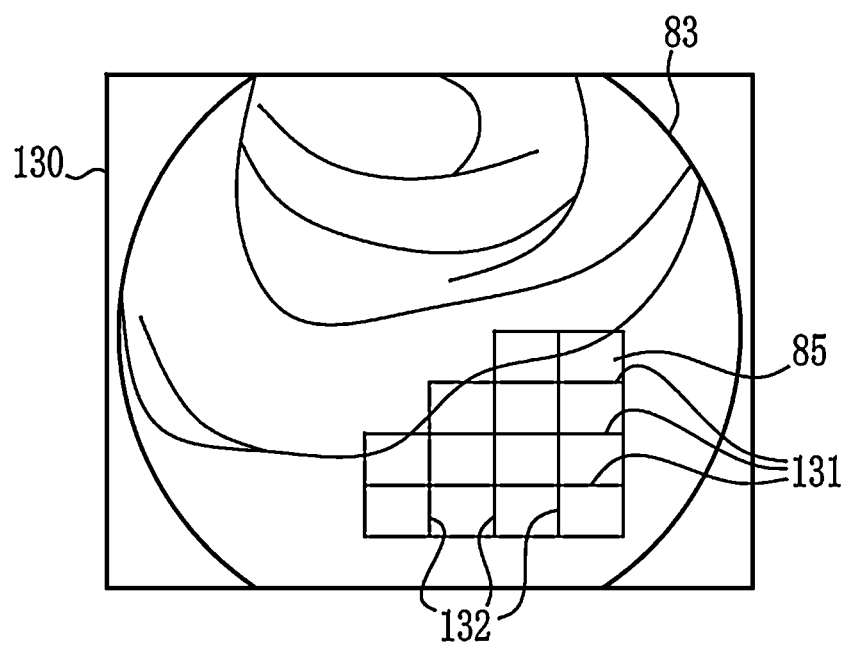
FIG. 11 illustrates a display image in a display form in which a plurality of textures are joined together.

More specifically, as illustrated in FIG. 11, the texture processing unit 73 can generate a biological information image 130 by using, for example, the tile textures 85. The biological information image 130 is a biological information image obtained by superimposing the plurality of tile textures 85 on the display image 81. Here, the texture processing unit 73 superimposes the tile textures 85 on the display image 81 while changing the size of the tile textures 85 to generate the biological information image 130. Accordingly, in the biological information image 130, no gap is present between the tile textures 85 adjacent to each other, and the tile textures 85 adjacent to each other share the outline. In a case where the tile textures 85 have an outline in a color different from the color of the inner part thereof, in the biological information image 130, the outlines of the tile textures 85 adjacent to each other are united to form transverse lines 131 and longitudinal lines 132. As a result, the transverse lines 131 and the longitudinal lines 132 show the boundaries between the tile textures 85 adjacent to each other.

As described above, in a case where textures are superimposed on a display image or the like such that adjacent textures share the outline, the boundary between the adjacent textures can be clearly shown by using textures having an outline in a color different from the color of the inner part thereof without providing a gap between the adjacent textures. As a result, biological information can be displayed so as to clearly indicate that the biological information is being displayed.

Figure 12:
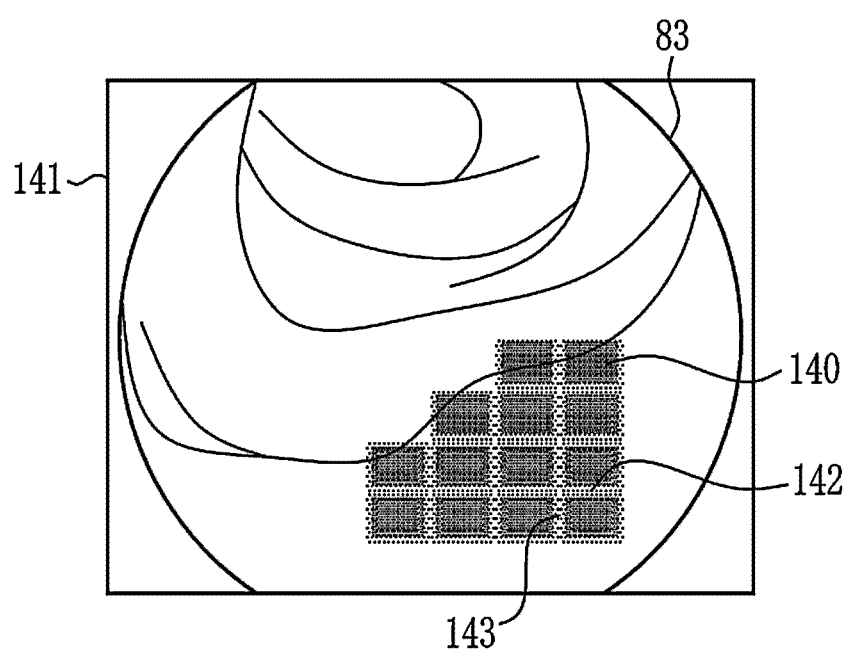
FIG. 12 illustrates a display image in which a boundary between adjacent textures is shown with the color of the textures.

Further, as illustrated in FIG. 12, the texture processing unit 73 can generate a biological information image 141 by using textures (hereinafter referred to as gradation textures) 140 having a gradation pattern in a color that changes, for example, from the center part to the peripheral part. The biological information image 141 is a biological information image obtained by superimposing the plurality of gradation textures 140 on the display image 81. In the biological information image 141, no gap is present between the gradation textures 140 adjacent to each other, and the gradation textures 140 adjacent to each other share the outline. The gradation textures 140 have a pattern in which the color of the center part and that of the peripheral part are different. Therefore, in the biological information image 141, the peripheral parts of the gradation textures 140 adjacent to each other are united to form boundary parts 142 and boundary parts 143 that are distinguishable from the center part of each gradation texture 140. As a result, in the biological information image 141, the boundary parts 142 and the boundary parts 143 substantially show the boundaries between the gradation textures 140 adjacent to each other.

As described above, in a case where textures are superimposed on a display image or the like such that adjacent textures share the outline, the boundary between the adjacent textures can be clearly shown by using textures having a pattern in which, for example, the color of the center part and that of the peripheral part are different without providing a gap between the adjacent textures. As a result, biological information can be displayed so as to clearly indicate that the biological information is being displayed.

Sixth Embodiment

Figure 13:
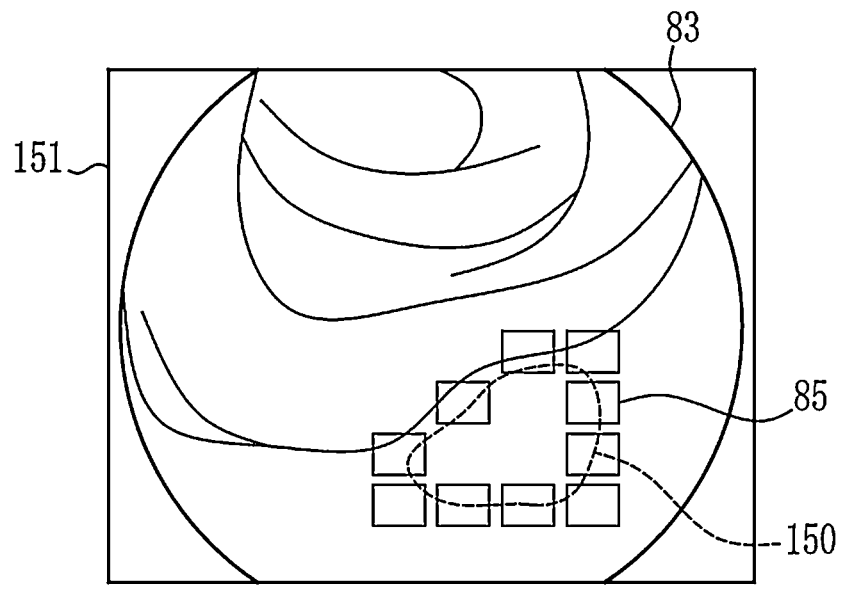
FIG. 13 illustrates a display image in a display form in which textures are superimposed on the basis of the rate of change of biological information.

In the first embodiment, the second embodiment, the third embodiment, the fourth embodiment, the fifth embodiment, and modifications thereof described above, the texture processing unit 73 displays values of biological information (oxygen saturation level) with textures. The texture processing unit 73 can display numerical value or the like that are, for example, calculated by using biological information, with textures. For example, as illustrated in FIG. 13, the texture processing unit 73 can generate a biological information image 151 that shows the outline of a part (hereinafter referred to as a lesion or the like) 150, which is, for example, a lesion or a potential lesion having a specific form. For example, the biological information image 151 is a biological information image obtained by superimposing the tile texture 85 on a part in which the rate of change of the oxygen saturation level is very high.

In a case where the biological information image 151 described above is generated, the texture processing unit 73 obtains the oxygen saturation level from the biological information calculation unit 72, and thereafter, differentiates the distribution of the oxygen saturation level to calculate the rate of change of the oxygen saturation level (hereinafter simply referred to as the rate of change) and performs superimposition determination similar to that in the first embodiment for the calculated rate of change. As the reference value for superimposition determination, a reference value determined in advance for the rate of change is used. On the basis of the result of superimposition determination, a texture is superimposed on the lattice point 82 that belongs to a region having a rate of change greater than or equal to the reference value and no texture is superimposed on the lattice point 82 that belongs to a region having a rate of change less than the reference value. Accordingly, the texture processing unit 73 generates the biological information image 151 described above.

When numerical values or the like that are, for example, calculated by using biological information are displayed with textures, display in a form different from a form in which values of biological information are displayed as is can be performed such that, for example, the outline of the lesion or the like 150 can be shown. In a case where the outline of the lesion or the like 150 is shown with textures as in the biological information image 151, for example, the presence and position of the lesion or the like 150 for which paying attention to its outline is important can be directly made known. For example, whether to make a diagnosis may be determined on the basis of whether the outline of the lesion or the like 150 is clear. In the biological information image 151, when the tile textures 85 are present so as to entirely surround the lesion or the like 150, it can be clearly known that the outline of the lesion or the like 150 is clear. In contrast, in a case where the tile textures 85 are not displayed in a part of the outline of the lesion or the like 150, it can be clearly known that the outline of the lesion or the like 150 is unclear in the part. In addition, when the outline of the lesion or the like is shown with textures as in the biological information image 151, the inner part (a part inside the outline) of the lesion or the like 150 can be observed in the original state in which textures are not superimposed, which is an advantage.

In this embodiment, the texture processing unit 73 superimposes a texture on a part in which the rate of change of biological information is greater than or equal to the reference value. The texture processing unit 73 can use "numerical values or the like that are, for example, calculated by using biological information" other than the rate of change, in superimposition determination. For example, the texture processing unit 73 can superimpose a texture on a part in which the difference or ratio between the reference value determined for biological information and the value of biological information calculated by the biological information calculation unit 72 satisfies a specific condition. In a case where the difference or ratio between the reference value and the value of biological information is used in superimposition determination as described above, the difference between the reference value and the value of biological information is highlighted unlike in a case where the value of biological information is used as is in superimposition determination. Accordingly, in a case of biological information that continuously changes, textures may be repeatedly displayed and hidden in a part of the photographic subject in which biological information has a value close to the reference value. However, when the difference or ratio between the reference value and the value of biological information is used in superimposition determination, such blinking of textures can be suppressed, and biological information may be stably displayed with textures.

Other Modifications and the Like

Figure 14:
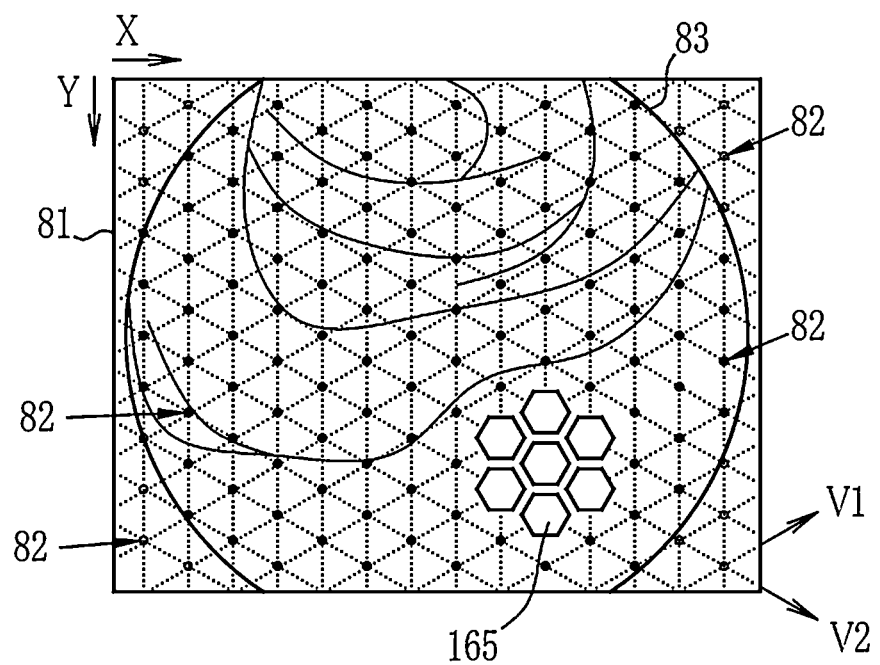
FIG. 14 is an explanatory diagram illustrating an example in which lattice points on each of which a texture can be superimposed are in a triangular lattice.

In the embodiments, modifications, and the like described above, although an example has been described where the lattice points 82 that are positions at each of which the texture processing unit 73 can superimpose a texture form a square lattice, the lattice points 82 can be arranged as desired. For example, as illustrated in FIG. 14, the texture processing unit 73 can set the lattice points 82 in a triangular lattice on the display image 81 in accordance with a setting or the like. In this case, it is preferable to use, as the textures, tile textures 165 having a hexagonal shape instead of the tile textures 85 having a rectangular shape. This is because when the tile textures 165 having a hexagonal shape are used, the tile textures 165 having a hexagonal shape can be spread over the lattice points 82 in a triangular lattice without any unwanted gap except a gap that is intentionally provided between adjacent textures. When the lattice points 82 in a triangular lattice are set, the tile textures 165 can be adjacent to one another in three directions, namely, the Y direction, the V1 direction, and the V2 direction, due to the arrangement of the lattice points 82. Accordingly, in a case where a gap is provided between the tile textures 165 adjacent to each other, the size of the gap between the tile textures 165 adjacent to each other in each of the Y direction, the V1 direction, and the V2 direction can be set. However, it is preferable that all of the gaps between the tile textures 165 adjacent to each other in these directions be equal to one another in order to prevent, for example, an unintended shape or pattern from appearing on the display image 81.

In the embodiments, modifications, and the like described above, although the texture processing unit 73 determines in advance the reference value used in superimposition determination for textures, the reference value used in superimposition determination for textures can be flexibly determined in accordance with the photographic subject that is an observation target. For example, in a case where the oxygen saturation level is used as biological information, for example, the oxygen saturation level that is calculated for a part specified by, for example, a doctor who is an operator of the endoscope system 10 can be employed as the reference value for superimposition determination. Although a value of the oxygen saturation level that can be regarded as normal varies depending on the photographic subject, when the reference value is flexibly set in accordance with the photographic subject as described above, superimposition determination suitable to the photographic subject can be performed.

In the embodiments, modifications, and the like described above, the texture processing unit 73 may superimpose a texture on every lattice point 82 present within the photographic subject display area 83 depending on the result of superimposition determination. However, in a case where, for example, the photographic subject is enlarged and observed, when a texture is superimposed on every lattice point 82 present within the photographic subject display area 83, display of the textures may be troublesome depending on the photographic subject or the observation form of the photographic subject. Accordingly, it is preferable that the texture processing unit 73 specify an upper limit to an area, on a display image or the like, for which textures can be superimposed (the maximum value of an area, on a display image or the like, occupied by textures) and superimpose textures as long as the area of a region in which textures are superimposed is less than or equal to the upper limit. This can prevent a situation where textures completely cover the photographic subject display area 83. Further, display of textures can facilitate recognition of a region to which attention is to be specifically paid. In a case where the total area of textures to be superimposed exceeds the upper limit as a result of superimposition determination for each lattice point 82, the texture processing unit 73 stops superimposing textures from a texture corresponding to the lattice point 82 for which, for example, the value of biological information is closer to the reference value. For example, in the example in the first embodiment, the texture processing unit 73 sequentially stops superimposing textures from a part having an oxygen saturation level closer to a normal value. This is because superimposing a texture on the lattice point 82 for which, for example, the value of biological information deviates from the reference value is more likely to contribute to, for example, a diagnosis than superimposing a texture on the lattice point 82 for which, for example, the value of biological information is closer to the reference value.

In the embodiments, modifications, and the like described above, although display of biological information with textures is continuously performed, it is preferable that the texture processing unit 73 stop the process for superimposing textures in a case where motion of the photographic subject in a display image or the like stops or in a case where motion of the endoscope 12 (specifically, the insertion part 12a inserted into the photographic subject) that captures a display image or the like stops. In a case where no motion is observed for the photographic subject or the endoscope 12, for example, a doctor who is an operator of the endoscope system 10 may desire to closely examine a part that the doctor is observing at that time. Therefore, the process for superimposing textures is stopped in such a case in order to prevent display of textures from actually hindering, for example, the diagnosis. Note that "stopping" of motion of the photographic subject or the endoscope 12 means that, for example, the amount or speed of motion of the photographic subject or the endoscope 12 is less than or equal to a specific threshold value, and includes a state where the photographic subject or the endoscope 12 almost stops substantially (moves to a small degree) in addition to a state where the photographic subject or the endoscope 12 completely stops. As long as the functions of the texture processing unit 73 are not stopped by a setting or the like, the texture processing unit 73 restarts the process for superimposing textures when the photographic subject or the endoscope 12 starts moving again after the photographic subject or the endoscope 12 stops moving.

Figure 15:
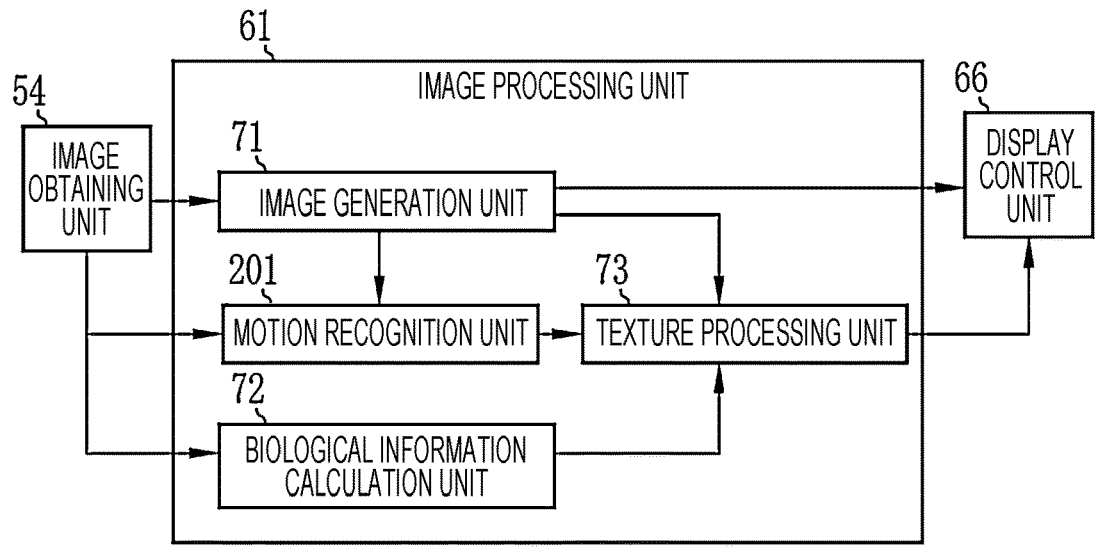
FIG. 15 is a block diagram of the image processing unit that includes a motion recognition unit.

As described above, in a case where, for example, the process for superimposing textures is stopped in accordance with motion of the photographic subject or the endoscope 12, as illustrated in FIG. 15, the image processing unit 61 is provided with a motion recognition unit 201. The motion recognition unit 201 obtains a display image or the like from the image obtaining unit 54 and/or the image generation unit 71. The motion recognition unit 201 uses the display image or the like to recognize motion of the photographic subject or the endoscope 12. As the method for the motion recognition unit 201 to specifically recognize motion, any publicly known method, such as calculation of a motion vector, can be used. Further, the motion recognition unit 201 inputs the results of recognition of, for example, the presence or absence, amount, and/or speed of motion of the photographic subject or the endoscope 12 to the texture processing unit 73. The texture processing unit 73 stops or starts (restarts) the process for superimposing textures on a display image or the like in accordance with the results of recognition by the motion recognition unit 201.

Figure 16:
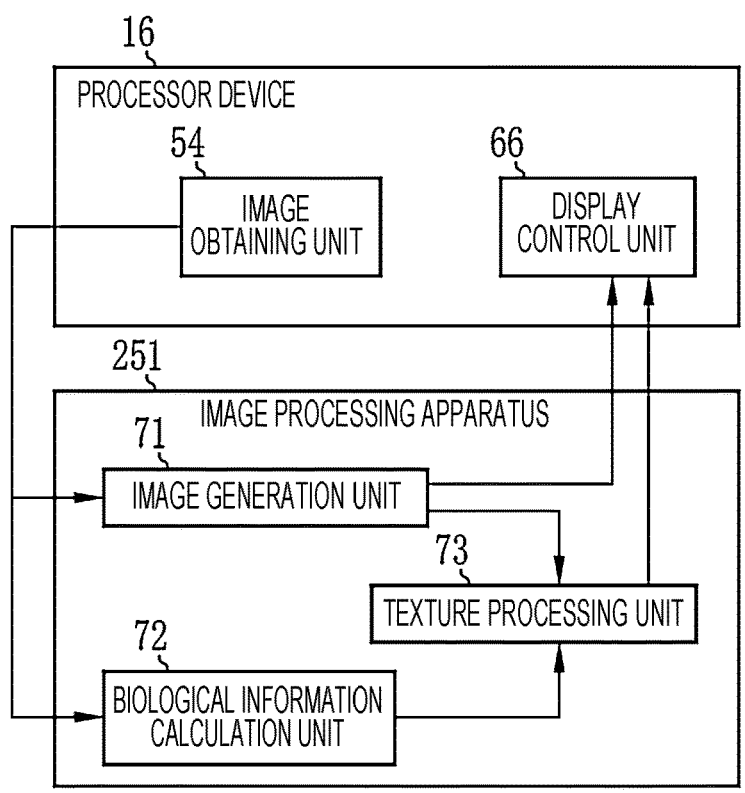
FIG. 16 is a block diagram of an image processing apparatus separate from a processor device.

In the embodiments, modifications, and the like described above, although the processor device 16 functions as an image processing apparatus, as illustrated in FIG. 16, an image processing apparatus 251 that includes the image generation unit 71, the biological information calculation unit 72, and/or the texture processing unit 73 can be provided separately from the processor device 16.

Figure 17:
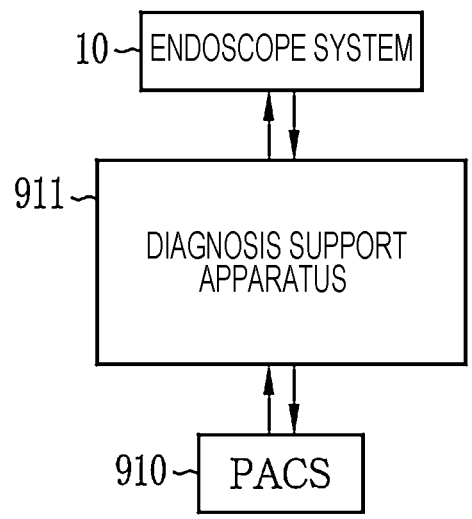
FIG. 17 is an explanatory diagram of a diagnosis support apparatus.
Figure 18:
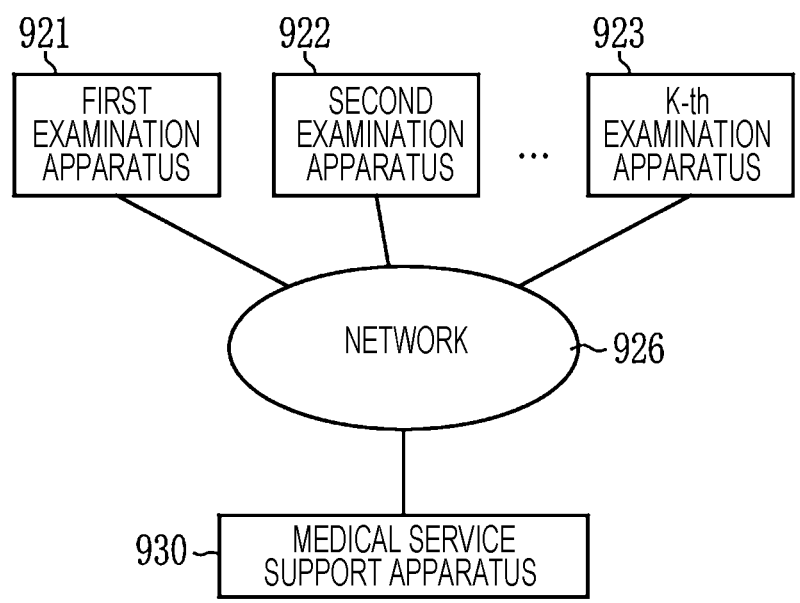
FIG. 18 is an explanatory diagram of a medical service support apparatus.

In addition, as illustrated in FIG. 17, the image generation unit 71, the biological information calculation unit 72, and/or the texture processing unit 73 can be provided in, for example, a diagnosis support apparatus 911 that obtains raw images captured by the endoscope 12 directly from the endoscope system 10 (including one that does not have, for example, the texture processing unit 73) or indirectly from a PACS (Picture Archiving and Communication Systems) 910. Further, as illustrated in FIG. 18, the image generation unit 71, the biological information calculation unit 72, and/or the texture processing unit 73 can be provided in a medical service support apparatus 930 that is connected, via a network 926, to various examination apparatuses, such as a first examination apparatus 921, a second examination apparatus 922, . . . , a K-th examination apparatus 923, that include the endoscope system 10.

Some or all of the embodiments and modifications described above can be combined and implemented as desired. In the embodiments and modifications described above, although a soft endoscope having the insertion part 12*a* that is flexible is used as the endoscope 12, the present invention is suitable also to a case of using a capsule endoscope that is swallowed by a photographic subject and used or a hard endoscope (laparoscope) used in, for example, a surgical operation.

The embodiments, modifications, and the like described above include an image processing method and an operation method for an endoscope system, the methods including: a step of obtaining, by the image obtaining unit, an endoscopic image obtained by capturing an image of a photographic subject; a step of calculating, by the biological information calculation unit, biological information concerning the photographic subject by using the endoscopic image or a display image generated by using the endoscopic image; and a step of superimposing, by the texture processing unit, a plurality of textures representing the biological information on the endoscopic image or the display image and showing, by the texture processing unit, a boundary between adjacent textures.

In the embodiments, modifications, and the like described above, the hardware configuration of the processing units that perform various types of processing of, for example, the image generation unit 71, the biological information calculation unit 72, and the texture processing unit 73 is implemented as various processors as described below. The various processors include a CPU (central processing unit), which is a general-purpose processor executing software (program) to function as various processing units, a GPU (graphical processing unit), a programmable logic device (PLD), such as an FPGA (field-programmable gate array), which is a processor having a circuit configuration that is changeable after manufacture, and a dedicated electric circuit, which is a processor having a circuit configuration specifically designed to perform various types of processing.

One processing unit may be configured as one of the various processors or a combination of two or more processors of the same type or different types (for example, a plurality of FPGAs, a combination of a CPU and an FPGA, or a combination of a CPU and a GPU). Further, a plurality of processing units may be configured as one processor. As the first example of configuring a plurality of processing units as one processor, a form is possible where one or more CPUs and software are combined to configure one processor, and the processor functions as the plurality of processing units, a representative example of which is a computer, such as a client or a server. As the second example thereof, a form is possible where a processor is used in which the functions of the entire system including the plurality of processing units are implemented as one IC (integrated circuit) chip, a representative example of which is a system on chip (SoC). As described above, regarding the hardware configuration, the various processing units are configured by using one or more of the various processors described above.

Further, the hardware configuration of the various processors is more specifically an electric circuit (circuitry) in a form in which circuit elements, such as semiconductor elements, are combined.

Note that the present invention can be used in, for example, a system or an apparatus that obtains medical images (including moving images) other than endoscopic images as well as an endoscope system, a processor device, and other related apparatuses that, for example, obtain endoscopic images. For example, the present invention is applicable to ultrasonic examination apparatuses, X-ray imaging apparatuses (including CT (computed tomography) examination apparatuses and mammography apparatuses), and MRI (magnetic resonance imaging) apparatuses.

REFERENCE SIGNS LIST

10 endoscope system
12 endoscope
12*a* insertion part
12*b* operation part
12*c* bending part
12*d* tip part
12*e* angle knob
12*f* treatment tool insertion port
13 zoom operation part
14 light source device
16 processor device
18 monitor
19 console 20 light source unit
22 light source control unit
30a illumination optical system
30b imaging optical system
45 illumination lens
46 object lens
47 zoom lens
48 image sensor
52 control unit (processor)
54 image obtaining unit
56 DSP
58 noise reduction unit
59 conversion unit
61 image processing unit
66 display control unit
71 image generation unit
72 biological information calculation unit
73 texture processing unit
81 display image
82 lattice point
83 photographic subject display area
85 tile texture
91 biological information image
92 biological information image
93 biological information image
101 first-color texture
102 second-color texture
110 biological information image
111 first-size texture
112 second-size texture
120 biological information image
121 first-shape texture
122 second-shape texture
130 biological information image
131 transverse line
132 longitudinal line
140 gradation texture
141 biological information image
142 boundary part
143 boundary part
150 lesion or the like
151 biological information image
165 tile texture
201 motion recognition unit
251 image processing apparatus
910 PACS
911 diagnosis support apparatus
921 first examination apparatus
922 second examination apparatus
923 K-th examination apparatus
926 network
930 medical service support apparatus

What is claimed is:
1. An image processing apparatus comprising a processor, the processor being configured to:
obtain an endoscopic image obtained by capturing an image of a photographic subject;
calculate biological information concerning the photographic subject by using the endoscopic image or a display image generated by using the endoscopic image; and
superimpose a plurality of textures representing a part including the biological information satisfying a specific condition on the endoscopic image or the display image and show a boundary between adjacent textures,
wherein the processor is further configured to:
provide a gap between adjacent textures; and
specify an upper limit to an area for which the textures are allowed to be superimposed, and to superimpose the textures as long as an area of a region in which the textures are superimposed is less than or equal to the upper limit.

2. The image processing apparatus according to claim 1, wherein the textures each have a size corresponding to two pixels or more.

3. The image processing apparatus according to claim 1, wherein the processor is further configured to superimpose the textures having colors that correspond to the biological information on the endoscopic image or the display image.

4. The image processing apparatus according to claim 1, wherein the processor is further configured to superimpose the textures having sizes that correspond to the biological information on the endoscopic image or the display image.

5. The image processing apparatus according to claim 1, wherein the processor is further configured to superimpose the textures having shapes that correspond to the biological information on the endoscopic image or the display image.

6. The image processing apparatus according to claim 1, wherein the processor is further configured to superimpose a texture on a part that satisfies a specific condition and superimpose no texture on a part that does not satisfy the specific condition.

7. The image processing apparatus according to claim 6, wherein the processor is further configured to superimpose a texture on a part in which a difference or ratio between a reference value determined for the biological information and a value of the calculated biological information satisfies the specific condition.

8. The image processing apparatus according to claim 6, wherein the processor is further configured to superimpose a texture on a part in which a rate of change of the biological information is greater than or equal to a reference value.

9. The image processing apparatus according to claim 1, wherein the processor is further configured to set positions at each of which a texture is allowed to be superimposed to fixed positions on the endoscopic image or the display image.

10. The image processing apparatus according to claim 1, wherein the processor is further configured to stop a process for superimposing the textures in a case where motion of the photographic subject in the endoscopic image or in the display image stops or in a case where motion of an endoscope that captures the endoscopic image or the display image stops.

* * * * *